United States Patent
Winningham

(10) Patent No.: US 7,322,692 B2
(45) Date of Patent: Jan. 29, 2008

(54) PROTECTIVE EYEWEAR WITH DETACHABLE FRAME

(75) Inventor: Matthew Winningham, Birmingham, MI (US)

(73) Assignee: Warrior Lacrosse, Inc., Warren, MI (US)

( * ) Notice: Subject to any disclaimer, the term of this patent is extended or adjusted under 35 U.S.C. 154(b) by 138 days.

(21) Appl. No.: 10/908,531

(22) Filed: May 16, 2005

(65) Prior Publication Data

US 2005/0254001 A1   Nov. 17, 2005

Related U.S. Application Data

(60) Provisional application No. 60/571,760, filed on May 17, 2004.

(51) Int. Cl.
*G02C 3/00* (2006.01)
(52) U.S. Cl. .......................... 351/156; 351/62; 351/157
(58) Field of Classification Search ............... 351/156, 351/157, 158, 62, 41; 2/426–429, 435–437, 2/431, 440, 448, 449
See application file for complete search history.

(56) References Cited

U.S. PATENT DOCUMENTS 6,276,795 B1 *   8/2001   Hall et al. .................... 351/62

OTHER PUBLICATIONS

DeBeer Vista Goggle.
Cascade Iris Goggle.
Brine Goggles.
Warrior Theia Wire Mask.

* cited by examiner

*Primary Examiner*—Hung Xuan Dang
(74) *Attorney, Agent, or Firm*—Dickinson Wright PLLC

(57) ABSTRACT

The present invention provides protective eyewear, also referred to as sport goggles, where the lens and the flexible frame are easily separated and interchangeable. The lens and the flexible frame are both available in a variety of colors. Therefore, the wearer can select and easily assemble a preferred color combination. More specifically, the protective eyewear includes a lens received within a flexible frame and a strap that is permanently attached to the lens for securing the eyewear to a wearer's face. There are at least two connection apertures spaced around an outer perimeter of the lens. The flexible frame has at least two connection protrusions that are aligned with the connection apertures in the lens for removably receiving the connection apertures.

8 Claims, 3 Drawing Sheets

PROTECTIVE EYEWEAR WITH DETACHABLE FRAME

CROSS-REFERENCE TO RELATED APPLICATIONS

The present invention claims priority from U.S. Provisional Application Ser. No. 60/571,760, filed May 17, 2004, and entitled "Protective Eyewear With Detachable Frame."

FIELD OF THE INVENTION

The present invention generally relates to protective eyewear. The present invention more particularly relates to protective eyewear for use during participation in a sporting activity such as lacrosse.

BACKGROUND OF THE INVENTION

Protective eyewear is well known for a variety of purposes and applications. For example, protective eyewear is utilized in factories as well as other manufacturing facilities to protect a wearer's eyes from injury. Indeed, certain government agencies have regulated that protective eyewear is required to be worn in most areas where manufacturing, assembly, and/or processing occurs. This protective eyewear typically consists of a one piece plastic portion for covering and protecting a wearer's eyes. Some known protective eyewear is intended to be secured to the wearer's head by an elastic strip. Other known protective eyewear is intended to engage a wearer's head by ear supports in the same fashion as do conventional eyeglasses. Most of this protective eyewear is relatively bulky as it is intended to fit over a wearer's normal eyeglasses if present.

Protective eyewear is also utilized to protect a wearer's eyes in sporting events, including women's lacrosse. The protective eyewear utilized for lacrosse typically consists of a frame surrounding an integral cage, which is intended to cover and protect a wearer's eyes. This protective eyewear suffers from various drawbacks, including the fact that it is relatively heavy, can impede a wearer's vision due to the bars of the cage, and is not readily replaceable if any portion of the protective eyewear is damaged.

To date, in some girl's or women's lacrosse organizations, the decision as to whether to wear protective eyewear during play is left up to the individual. However, for the 2005 season, the National Federation of State High School Associations has mandated eye protection for Girl's lacrosse. Therefore, it would be desirous to provide protective eyewear that overcomes some of the drawbacks present with existing protective eyewear. It would also be desirable to provide protective eyewear.

SUMMARY OF THE INVENTION

It is therefore an advantage of the present invention to provide protective eyewear that provides increased vision for a wearer.

It is another advantage of the present invention to provide protective eyewear that provides increased comfort for a wearer.

It is still another advantage of the present invention to provide protective eyewear that provides increased protection for a wearer.

It is a further advantage of the present invention to provide protective eyewear that allows for ready interchangeability of its components.

It is still a further advantage of the present invention to provide protective eyewear that is fashionable.

In accordance with the above and the other advantages of the present invention, protective eyewear, also referred to as sport goggles, for use during participation in a sporting activity is provided. In one embodiment, the lens and the flexible frame are easily separable. The lens and the flexible frames are both available in a variety of different colors. Therefore, the wearer can select and easily assemble a preferred color combination due to the interchangeability of the individual components.

More specifically, the protective eyewear includes a lens that is engageable with a flexible frame. The protective eyewear also includes a strap that is coupled to the lens for securing the eyewear around a wearer's head in a protective position on a wearer's face. The flexible frame has a front surface and a back surface. The back surface rests against the wearer's face while the front surface includes a depression for receiving the lens. Further, the back surface may have at least one ridge to provide a contoured fit around the wearer's face. The lens has a first eye section and a second eye section. The strap is fixedly attached to the single lens at both the first eye section and the second eye section.

There are at least two connection apertures spaced around an outer perimeter of the lens. The flexible frame has at least two connection protrusions in the depression that are alignable with the connection apertures in the lens for removably receiving the connection apertures.

Advantages, design considerations, and applications of the present invention will become apparent to those skilled in the art when the detailed description of the best mode contemplated for practicing the invention, as set forth herein below, is read in conjunction with the accompanying drawings.

BRIEF DESCRIPTION OF THE DRAWINGS

The present invention will be described, by way of example, with reference to the following drawings.

DETAILED DESCRIPTION OF THE PREFERRED EMBODIMENT

Figure 1:
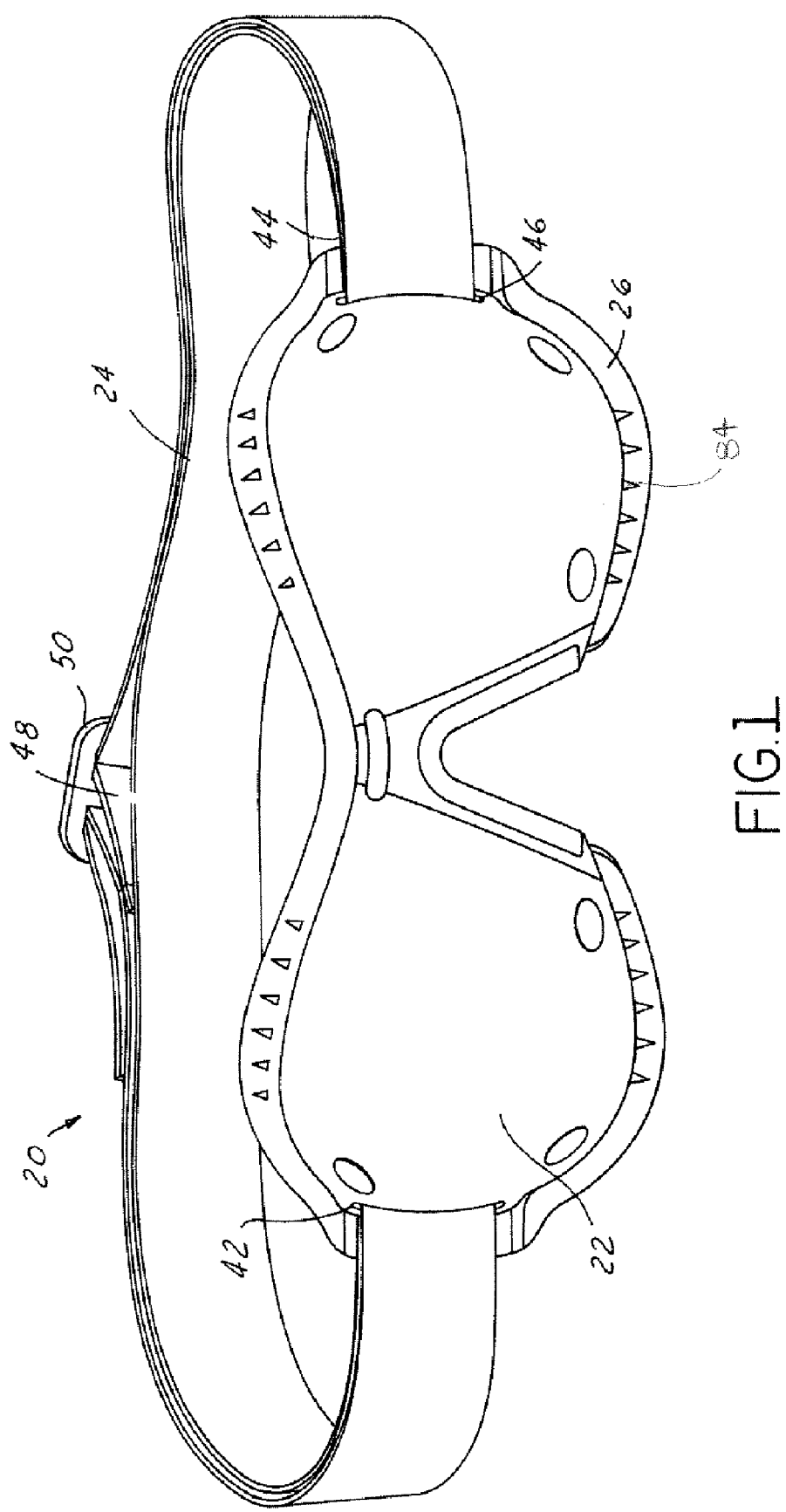
FIG. 1 illustrates a perspective view of protective eyewear in a fully assembled condition in accordance with one embodiment of the present invention.

Referring now to the Figures, FIG. 1 illustrates one embodiment of protective eyewear in accordance with the present invention. The protective eyewear 20 is preferably intended for the game of lacrosse and specifically for use by women. It will be understood, however, that the protective eyewear 20 can be utilized in a variety of different applications, including other sporting or athletic activities. The protective eyewear 20 is also not limited to use by women and may also be used by men. In this Figure, the protective eyewear 20, is shown in a fully assembled state. The protective eyewear 20 generally includes a single lens 22 which is coupled to a strap 24 to help secure the protective eyewear 20 to a wearer's head. The protective eyewear 20 also includes a flexible frame 26 removably attached to or engageable with the lens 22.

Figure 2:
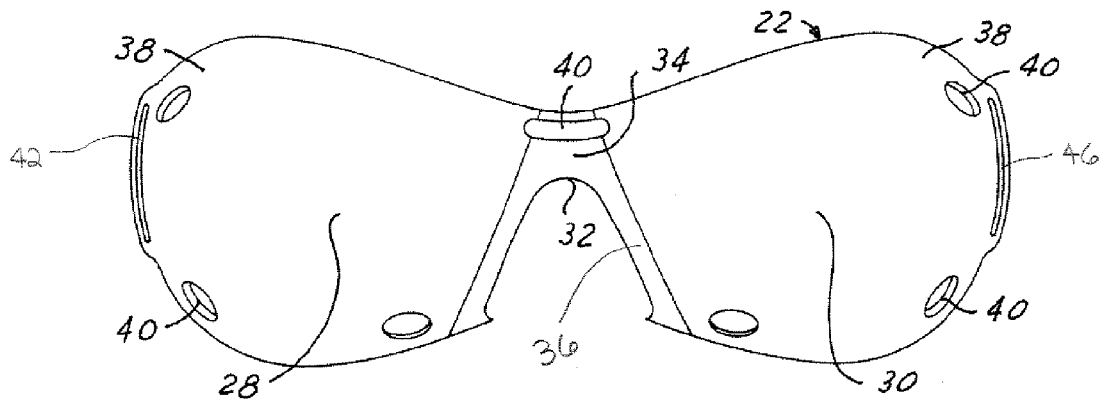
FIG. 2 illustrates a front view of the lens portion of the protective eyewear illustrated in FIG. 1.

Referring to FIG. 2, the single lens 22 has a first eye section 28 and a second eye section 30. The first eye section 28 is separated from the second eye section 30 by a recess 32, which is intended to receive a wearer's nose and defines a bridge section 34. The protective eyewear 20 also includes a bridge support 36 that is attached to the lens 22 between the first eye section 28 and the second eye section 30. More specifically, the bridge support 36 is located in the lens recess 32 and supports the eyewear 20 on the wearer's nose during use. The lens 22 is preferably constructed of a plastic material and preferably has a clear color. However, the lens 22 may be constructed of other suitable materials as desired. Additionally, the lens 22 may consist of a variety of different shades, i.e. it may be tinted for sun reflection or protection purposes. Further, the lens 22 may consist of multiple pieces instead of only a single piece.

The lens 22 may also have prescription characteristics, such that they act both as protective eyewear as well as a vision aid. Moreover, the lens 22 may have a coating such as a UV coating or anti-reflective coating.

As shown, the lens 22 has an outer perimeter 38. Located along the outer perimeter 38 of the lens 22 are at least two connection apertures 40 that are used for connecting the lens 22 to the flexible frame 26, as is discussed in more detail herein.

The strap 24 is preferably fixedly attached to the single lens 22 at both the first eye section 28 and the second eye section 30. The strap 24 is preferably permanently attached to the lens 22, however, the strap 24 may instead be releasably attached to the lens 22. Alternatively the strap 24 may be coupled to the frame 26. In one embodiment, the lens 22 has a first strap aperture 42 for receiving a first end 44 of the strap and a second strap aperture 46 for receiving a second end 48 of the strap. The first strap end 44 is inserted through the first strap aperture 42 and the second strap end 48 is inserted through the second strap aperture 46. The two strap ends 44, 48 are attached to each other via an adjustment buckle 50 that allows the wearer to adjust the tension of the eyewear 20 around the wearer's head for a tight fit. It will be understood that the strap ends 44, 48 may be secured to one another by a variety of other known suitable ways, including hook and loop attachments.

Figure 3:
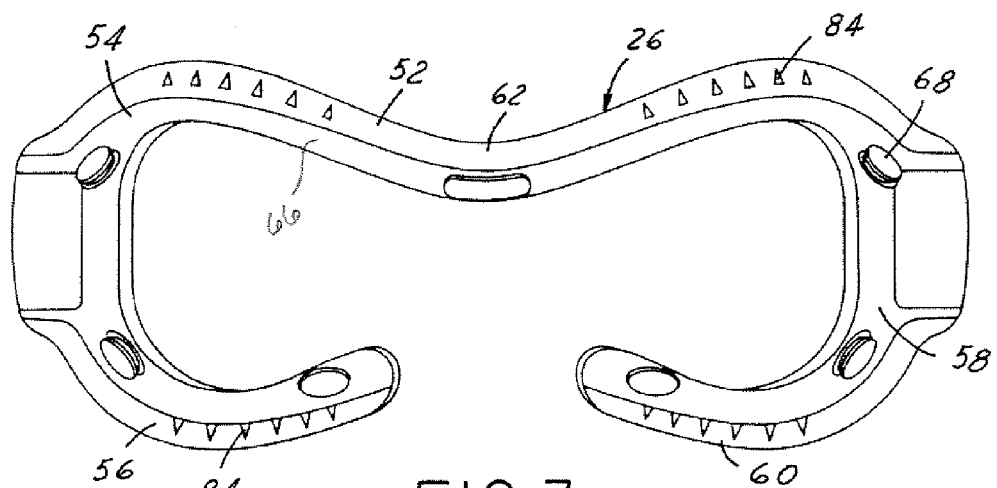
FIG. 3 illustrates a frontal view of the flexible frame illustrated in FIG. 1.
Figure 4:
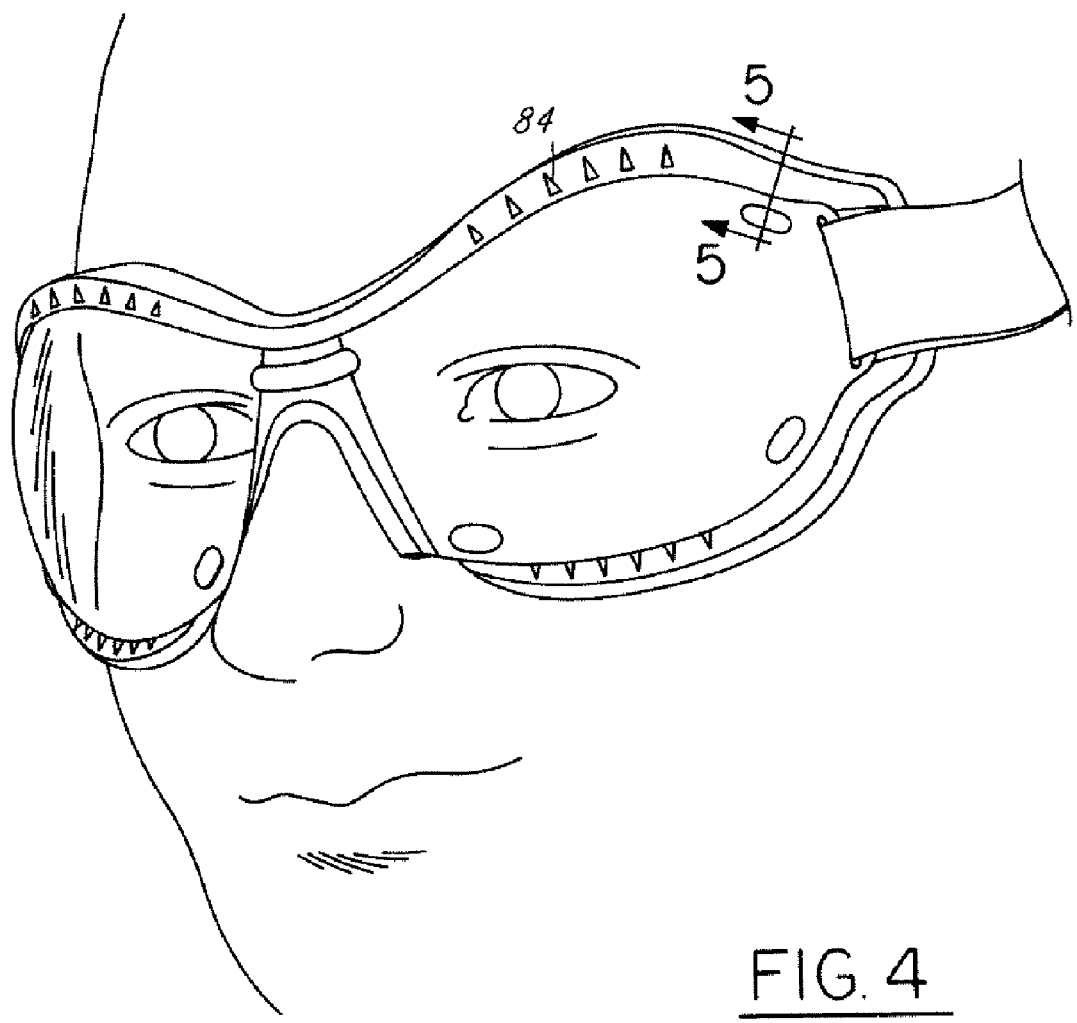
FIG. 4 illustrates a perspective view of the protective eyewear on a wearer's face in accordance with one embodiment of the present invention.

Referring to FIGS. 3 and 4, the flexible frame 26 includes an upper edge 52, a first side section 54, a first lower edge 56, a second side section 58 and a second lower edge 60. In other words, in one embodiment, the lower edge is discontinuous. When the protective eyewear 20 is being worn by a wearer, the upper edge 52 extends along the wearer's forehead above the eyes. The first side section 54 extends generally downward from the upper edge 52 into engagement with the first lower edge 56. Similarly, the second side section 58 extends generally downward from the upper edge 52 into engagement with the second lower edge 60. While the lower edge 56 is preferably discontinuous, the frame 26 may alternatively extend around or largely around the entire periphery of the lens 22 in a continuous fashion. Further, the frame 26 may be found in a variety of different configurations and may consist of multiple sized pieces as desired.

Figure 7:
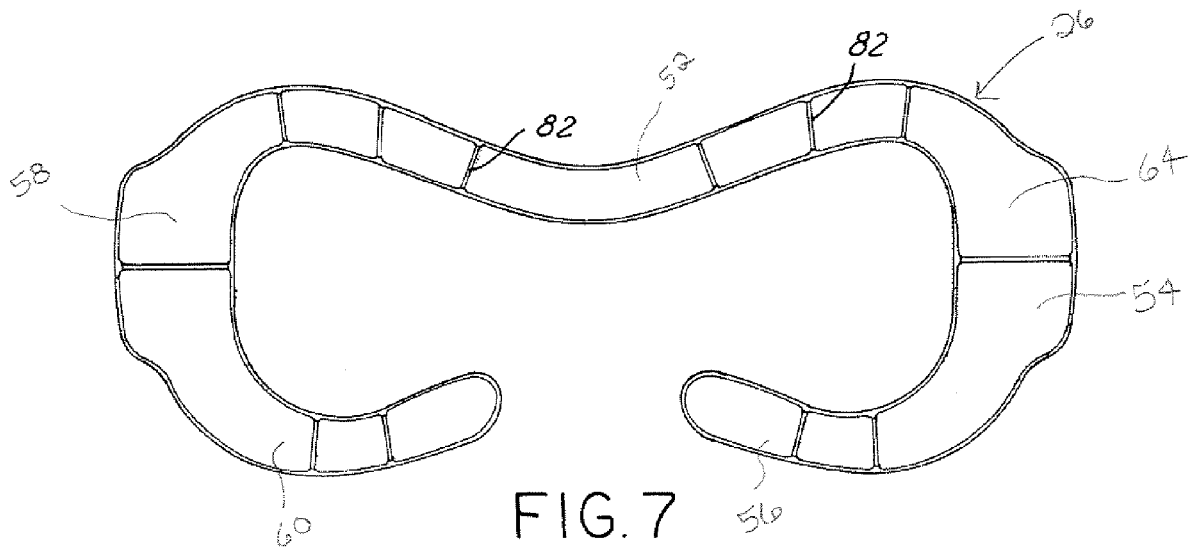
FIG. 7 illustrates a back view of the flexible frame portion of the protective eyewear illustrated in FIG. 1.

Further, the flexible frame 26 has a front surface 62 and a back surface 64, as illustrated in FIGS. 3, 4 and 7. The front surface 62 includes the surfaces of the upper edge 52, the first side section 54, the first lower edge 56, the second side section 58, and the second lower edge 60 that face away from the wearer's face when being worn. Conversely, the back surface 64 includes the surfaces of the upper edge 52, the first side section 54, the first lower edge 56, the second side section 58, and the second lower edge 60 that rest on or are oriented closer to the wearer's face when being worn.

The flexible frame front surface 62 includes a depression 66 for receiving the outer perimeter 38 of the single lens. Also, located in the depression 66 are a plurality of connection protrusions 68 that are alignable with the connection apertures 40 and removably receive the connection apertures 40. In one embodiment, the flexible frame 26 includes seven connection protrusions 68 and the lens 22 includes seven connection apertures 40 that are alignable with and removably receive the connection protrusions 68. In this embodiment, the location of the protrusions on the flexible frame are as follows: 1) one in the center of the upper edge 52; 2) one at the intersection of the upper edge 52 with the first side section 54; 3) one at the intersection of the first side section 54 with the first lower edge 56; 4) one at the end of the first lower edge 56 near the bridge support 36; 5) one at the intersection of the upper edge 52 with the second side section 58; 6) one at the intersection of the second side section 58 with the second lower edge 60; and 7) one at the end of the second lower edge 60 near the bridge support 36. It will be understood that any number of protrusions 68 may be utilized to assist in securing the lens 22 to the frame. Further, the lens 22 may be secured to the frame 26 by a variety of other suitable ways. Moreover, the protrusions 68 or other securing mechanisms can be disposed in a variety of other locations.

The protrusions 68 are made from a more rigid material than the material used to form the flexible frame 26. Therefore, the protrusions 68 are preferably made separately and are attached to the flexible frame 26. However, the protrusions 68 may also be integrally formed with the frame 26.

Figure 5:
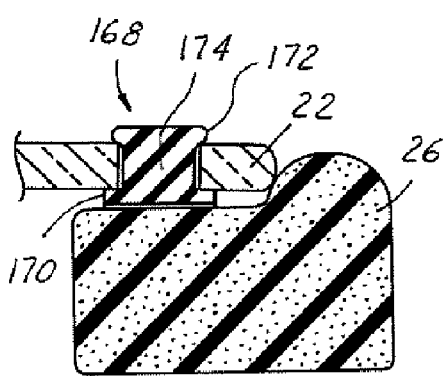
FIG. 5 illustrates a cross-sectional view of the flexible frame including one embodiment of a connection protrusion in accordance with the present invention.

In one embodiment, illustrated in FIG. 5, each protrusion 168 includes an inner lip 170, an outer lip 172 and a spacer 174 positioned between the inner and outer lips 170, 172. The inner lip 170 is adhered to the flexible frame 26 via the use of an adhesive or other suitable attaching mechanism. Further, the spacer 174 is received in the lens connection aperture 40 to secure the lens 22 and the flexible frame 26 together.

Figure 6:
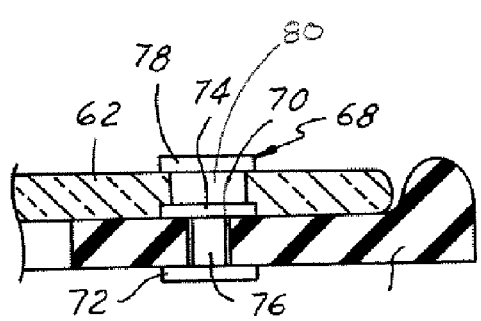
FIG. 6 illustrates a cross-sectional view of the flexible frame including another embodiment of a connection protrusion in accordance with the present invention.

Referring to FIG. 6, in another embodiment, each protrusion 68 is received in an opening 70 in the flexible frame 26 that is aligned with each connection aperture 40 in the single lens 22. Each protrusion 68 includes an inner lip 72, an intermediate lip 74, a first spacer 76 positioned between the inner lip 76 and intermediate lip 74, an outer lip 78 and a second spacer 80 that is positioned between the intermediate lip 74 and the outer lip 78. Preferably, the second spacer 80 has a larger cross-section than the first spacer 76 and is generally oval-shaped. The first spacer 76 is received in the opening 70 in the flexible frame 26 and the second spacer 80 is received in the single lens connection aperture 40. The connection protrusion 68 in the center of the upper edge 52 has a cross-section that is larger than the other connection protrusions to assist in providing a secure engagement.

As illustrated in FIG. 7, located on the back surface 64 of the flexible frame 26 is at least one relief cut ridge 82 to allow a contoured fit of the protective eyewear around the wearer's face during use, as illustrated in FIG. 7. In one embodiment, there are at least two relief cut ridges 82 on the upper edge 52, one relief cut ridge 82 on each side section 54, 58 and one relief cut ridge 82 on each lower edge section 56, 60. There may also be relief cut ridges on the front surface of the flexible frame, as illustrated in FIGS. 1, 3, and 4. It will be understood that more or less relief cut ridges may be utilized and that they may be located in a variety of different places on the frame.

The flexible frame 26 is preferably constructed of Ethylene Vinyl Acetate foam and the lens is preferably made from polycarbonate. The foam frame 26 is lightweight and therefore, advantageous. In one embodiment, the lens is coated with a scratch-proof material and/or also with a fog-proof material.

In one exemplary embodiment, the flexible frame has a maximum thickness of 0.55 inches, whereas the depression in the flexible frame has a maximum depth of 0.15 inches. The thickness of the lens is in the range of 0.11-0.14 inches. Obviously, the various thickness may vary.

The disclosed invention provides a substitutive lens and a substitutive flexible frame. Therefore, either the lens or the frame can be changed with minimal effort. This provides a variety of advantageous features. First, if either the frame or the lens 22 is damaged, such as a scratching of the lens 22, they can be readily detached from one another and the damaged component can be replaced. Additionally, like with anything else, color is important. The frame, which is preferably made of foam, can be formed in a variety of different colors. Whether a single solid color, multiple colors or a pattern. Thus, if a player wants to have a frame with a different color to match a jersey or for another reason, the interchangeability provides this capability. This interchangeability also allows a wearer to switch between a clear lens, for example, and a tinted lens to account for weather conditions. This can be done before a game or even during a game easily. Since both the lens and the frame are available in a variety of colors, the result is a customized product for each wearer.

While the present invention has been described in what is presently considered to be its most practical and preferred embodiment or implementation, it is to be understood that the invention is not to be limited to the disclosed embodiment. On the contrary, the present invention is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. Protective eyewear comprising:
    a single lens having a first eye section, a second eye section, and at least two connection apertures disposed around an outer perimeter, thereof;
    a strap fixedly attached to said first eye section of said lens and said second eye section of said lens to allow the eyewear to be maintained or a wearer's head; and
    a flexible frame having a front surface including a depression for receiving the outer perimeter of said single lens and at least two connection protrusions located in said depression that are aligned with said connection apertures and removably receive said connection apertures.

2. The eyewear according to claim 1, further comprising a bridge support attached to said lens between said first eye section and said second eye section.

3. The eyewear according to claim 1, wherein said flexible frame has a back surface including at least one relief cut ridge.

4. The eyewear according to claim 1, wherein said lens further comprises two strap apertures for receiving said strap.

5. The eyewear according to claim 1, wherein each said protrusion is a separate component and includes an inner lip, an intermediate lip, a first spacer positioned between said inner lip and said intermediate lip, an outer lip, and a second spacer that is positioned between the intermediate lip and the outer lip.

6. The eyewear according to claim 5, wherein said flexible frame includes an opening for each said connection protrusion wherein each said opening is aligned with each said single lens connection aperture.

7. The eyewear according to claim 1, wherein said flexible frame is made from Ethylene Vinyle Acetate foam.

8. The eyewear according to claim 1, wherein said lens is made from polycarbonate.

* * * * *